(12) United States Patent  (10) Patent No.: US 7,271,301 B2
Gelblum et al.  (45) Date of Patent: Sep. 18, 2007

(54) SYNTHESIS OF PERFLUOROOLEFINS

(75) Inventors: Peter Gideon Gelblum, Philadelphia, PA (US); Norman Herron, Newark, DE (US); Charles Joseph Noelke, Wilmington, DE (US); Velliyur Nott Mallikarjuna Rao, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/359,807

(22) Filed: Feb. 22, 2006

(65) Prior Publication Data

US 2006/0142622 A1 Jun. 29, 2006

Related U.S. Application Data

(63) Continuation of application No. 09/878,540, filed on Jun. 11, 2001, now abandoned.

(60) Provisional application No. 60/271,387, filed on Feb. 26, 2001, provisional application No. 60/218,338, filed on Jul. 14, 2000.

(51) Int. Cl.
  *C07C 17/02* (2006.01)
(52) U.S. Cl. ............... 570/153; 570/155; 570/156; 570/157; 570/158
(58) Field of Classification Search ........... 570/155, 570/156, 157, 158, 153
  See application file for complete search history.

(56) References Cited

U.S. PATENT DOCUMENTS

| 2,230,654 | A | 2/1941 | Plunkett |
| 2,394,243 | A | 2/1946 | Joyce, Jr. |
| 2,551,573 | A | 5/1951 | Downing et al. |
| 2,758,138 | A | 8/1956 | Nelson |
| 2,970,176 | A | 1/1961 | Ten Eyck et al. |
| 3,183,277 | A | 5/1965 | Scherer et al. |
| 3,306,940 | A | 2/1967 | Halliwell |
| 3,397,248 | A | 8/1968 | Hummel et al. |
| 3,446,858 | A | 5/1969 | Shingu et al. |
| 3,459,818 | A | 8/1969 | Ukihashi et al. |
| 3,873,630 | A | 3/1975 | West |
| 5,334,783 | A | 8/1994 | Freudenreich et al. |
| 5,516,947 | A | 5/1996 | Manogue et al. |
| 5,705,719 | A | 1/1998 | Bloos et al. |
| 6,624,337 | B1 * | 9/2003 | Manzer et al. ............... 570/153 |

FOREIGN PATENT DOCUMENTS

| EP | 0 337 127 | 3/1989 |
| GB | 1062768 | 3/1967 |
| WO | WO94/06554 | 3/1994 |
| WO | WO95/24369 | 9/1995 |

* cited by examiner

*Primary Examiner*—Shailendra Kumar

(57) ABSTRACT

A gold-lined pyrolysis reactor is used to pyrolyze compounds to form fluoroolefins like tetrafluoroethylene and hexafluoropropylene in high yield, with minimum to no formation of perfluoroisobutylene, chlorotrifluoroethylene, coke, salts, or polymer.

14 Claims, No Drawings

SYNTHESIS OF PERFLUOROOLEFINS

This application is a CON of Ser. No. 09/878,540, filed Jun. 11, 2001 now abandoned, which claims benefit of 60/218,338, filed Jul. 14, 2000 and claims benefit of 60/271,387, filed Feb. 6, 2001.

FIELD OF THE INVENTION

This invention relates to the synthesis of perfluoroolefins, including tetrafluoroethylene and hexafluoropropylene by pyrolysis of fluorinated compounds.

BACKGROUND OF THE INVENTION

Tetrafluoroethylene (TFE) and hexafluoropropylene (HFP) are important monomers in the preparation of fluoropolymers. TFE is commercially prepared by pyrolyzing $CHClF_2$ (CFC-22) (U.S. Pat. No. 2,551,573). Hexafluoropropylene is commercially prepared by pyrolyzing TFE (U.S. Pat. No. 2,758,138). Thus on a commercial basis, the TFE and HFP are prepared sequentially. HFP is disclosed in other patents as being preparable by pyrolysis of a wide variety of fluorocarbons, e.g. a mixture of TFE and saturated fluorocarbon or $C_4$ to $C_{10}$ fluoroolefin (U.S. Pat. No. 2,970,176), TFE/carbon dioxide mixture (U.S. Pat. No. 3,873,630), 2-chloro-1,1,1,3,3,3-hexafluoropropane (U.S. Pat. No. 3,397,248), TFE, perfluorocyclobutane, or mixtures thereof, all in the presence of excess superheated steam (U.S. Pat. No. 3,446,858), and chlorotetrafluoroethane and/or chlorohexafluoropropane or a mixture of chlorotetrafluoroethane with perfluorocyclobutane (EP 0 337 127 A1). TFE and HFP are reported to be preparable simultaneously, i.e. co-synthesized, by pyrolyzing
a) chlorodifluoromethane to a mixture of TFE and HFP (U.S. Pat. No. 3,306,940),
b) a mixture of chlorodifluoromethane and 1,1,1,2-tetrafluoro-2-chloroethane (British Patent 1,062,768), or
c) a mixture of chlorodifluoromethane and TFE formed by partial pyrolysis of chlorodifluoromethane to TFE, followed by removal of HCl (U.S. Pat. No. 3,459,818).

U.S. Pat. No. 5,334,783 discloses a process for the preparation of hexafluoropropylene by thermal cleavage which uses a mixture (e.g., an azeotropic mixture) of chlorotetrafluoroethane and perfluorocyclobutane. Various reactor wall materials are mentioned including "platinum or similar noble metals". The use of a platinum-tube reactor is exemplified. This patent suggests that where mixtures of chlorotetrafluoroethane isomers are employed, the ratio of $CHClFCF_3$ to $CHF_2CClF_2$ is preferably not more than 1:4.

The prior art describing materials of construction for pyrolysis reactors used for producing TFE and HFP is non-specific, except that the material of construction has to withstand the reaction conditions and the chemical action of the reactants and reaction products. U.S. Pat. No. 3,306,940 discloses noble metals, silver, carbon, and Inconel® alloy, which is a nickel alloy. U.S. Pat. No. 2,551,573 compares performance in a carbon tube with and without a coil of gold wire in the reaction zone: the conversion rate and the product composition is the same in both cases. Inconel® alloy, because it is lower in cost than such metals as platinum and silver and lends itself to periodic cleaning to remove coke and/or polymer deposits, has become a standard material of construction for the pyrolysis reactor.

All of these processes can suffer from one or more of the problems of salts, of coke and/or polymer forming in the tubular pyrolysis reactor, eventually plugging the reactor and causing it to be shut down for cleaning, and of excessive by-product formation. These byproducts include perfluoroisobutylene (PFIB) (U.S. Pat. No. 5,705,719), which is toxic, and $CF_2$=CFCl(CFC-1113), which is also undesirable in the process. Other products observed in some of these processes include the cyclic dimer of tetrafluoroethylene, namely perfluorocyclobutane, and 2-chloro-1,1,2,2-tetrafluoroethane. The sequential processes, i.e. first make TFE and then convert the TFE to HFP, while tending to provide high yields of these desirable perfluoroolefins, have the disadvantage of the extra expense of sequential operation and high production of the toxic PFIB and by-products in the second stage, plugging of the pyrolysis pipes/tubes and their high rate of erosion/corrosion causing low onstream efficiency and costly maintenance and shutdowns.

It is desirable to develop a reactor and a process for pyrolyzing fluoromonomer reactants for fluoropolymer production by which increased levels of such fluoromonomers are produced, while also reducing levels of undesirable by-products such as coke, polymer and PFIB.

SUMMARY OF THE INVENTION

The present invention provides a pyrolysis process for the co-synthesis of tetrafluoroethylene, hexafluoropropylene, and other fluoromonomers that solves these problems, i.e. providing the economic advantage of simultaneous production of HFP and TFE, and either reducing or eliminating both a) plugging of the pyrolysis reactor and b) the formation primarily of PFIB and $CF_2$=CFCl and other by-products. It has been discovered that the selection of gold as a component of at least the reaction zone of the pyrolysis reactor provides this result.

In one embodiment, the present invention is a reactor for the pyrolysis of reactants that can produce fluoromonomers, said reactor comprising a reaction zone, the surface of which reaction zone comprises gold.

In a second embodiment, the present invention is a reactor for the pyrolysis of reactants that can produce fluoromonomers, said reactor comprising a reaction zone and a quench zone, the surfaces of which comprise gold.

A third embodiment of this invention is a process comprising feeding at least one reactant which can produce fluoromonomers into a reactor having a reaction zone, the surface of which reaction zone comprises gold, under conditions sufficient to produce fluoromonomers, including tetrafluoroethylene and hexafluoropropylene.

In a fourth embodiment, the present invention is a process for the pyrolysis of reactants that can produce fluoromonomers, such as TFE and HFP, wherein the reactant is at least one compound selected from the group consisting of compounds that can provide a $CF_2$: moiety, a $CF_3CF$: moiety, and a $CF_2CF_2$: moiety. For simplicity, the unsatisfied valences of these moieties are shown as ":" at the end of the moiety. This representation is similar to that used for divalent carbon moieties known as carbenes. As used here, this representation does not exclude carbenes, and is not limited to carbenes.

In a fifth embodiment, the present invention is a process for the pyrolysis of reactants that can produce fluoromonomers, such as TFE and HFP, wherein said reactants are a mixture of a monocarbon compound that can provide the $CF_2$: moiety together with a) a dicarbon compound selected from the group consisting of compounds that can provide the $CF_3CF$: moiety and the $CF_2CF_2$: moiety, and tetrafluoroethylene, and/or b) perfluorocyclobutane.

A sixth embodiment of this invention is a process for producing at least one fluoroolefin selected from the group consisting of tetrafluoroethylene and hexafluoropropylene, comprising: pyrolyzing a gaseous feed containing $C_2HClF_4$ and perfluorocyclobutane at a temperature of from about 600° C. to about 1000° C. in a reactor wherein surfaces exposed to said pyrolysis are gold; wherein a molar ratio of $C_2HClF_4$ to perfluorocyclobutane in said feed is from about 1:10 to about 10:1, and a molar ratio of $CHClFCF_3$ to $CHF_2CClF_2$ in said feed is at least about 1:1.

The temperature and residence time of the feed compound(s) are chosen such that the yield to TFE and HFP combined is preferably at least about 85%. The term "yield" as used herein is the total number of carbon atoms in the products, divided by the total number of carbon atoms in the feed to the pyrolysis reactor. The term "selectivity" as used herein is the total number of carbon atoms in the products, divided by the total number of carbon atoms in that fraction of the feed that is converted by pyrolysis. By "products" is meant the identified perfluoroolefins or other identified fluorinated organic compounds exclusive of the compounds fed to the reactor.

The term "fluoromonomer" as used herein includes, but is not limited to TFE and HFP.

Contrary to the previous experience in pyrolyzing compounds to make fluoromonomer in reactors made of materials other than gold, we have now found that with gold as a material of construction in the reaction zone of the reactor has a very beneficial effect on the reaction as will be described hereinafter.

DETAILED DESCRIPTION

Pyrolysis, as the term is used herein, means chemical change produced by heating. However, it is not the intention of the inventors to speculate upon the mechanism of reactions that take place in pyrolysis. When more than one reactant is present during pyrolysis, only one may be changed by heat and the product or products of that change may react with one or more of the reactants. On the other hand, more than one of the reactants may change under heating before reacting further, if further reaction takes place.

Pyrolysis reactors generally comprise three zones: a) a preheat zone, in which reactants are brought close to the reaction temperature; b) a reaction zone, in which reactants reach reaction temperature and are at least partially pyrolyzed, and products and any byproducts form; c) a quench zone, in which the stream exiting the reaction zone is cooled to stop the pyrolysis reaction.

The present invention embodies the discovery that gold as a material of the surface in the reactor, contributes something more to the reaction than simply resistance to the reaction conditions and chemicals: The ability to reduce or eliminate both the formation of salts and of coke on the exposed reactor surface, as well as to reduce the production of PFIB and $CF_2$=CFCl as described above and reduce formation of polymer in the quench zone.

A study of the effects of the pyrolysis reaction on the materials of construction has been performed in a thermogravimetric analyzer (TGA). By suspending a coupon of the metal in question from the balance arm of the TGA, weight changes as a consequence of the gas phase pyrolysis reaction can be followed. While gold consistently shows little weight change during the reaction, Inconel® shows first weight decrease, consistent with corrosion to form volatile salts, and then a large weight increase, due to heavy coke build up. Post-reaction analysis shows a thick layer of coke deposit as well as evidence of sublimed metal chloride salts at the cool exit end of the TGA reactor. Details will be found in the Examples. Even platinum and palladium, usually referred to as noble metals, are inferior to gold in that they produce more by-products and/or larger amounts of the toxic PFIB as shown in the Examples. These improvements in operation justify the preferred use of gold on the exposed surface of the reaction zone and optionally on the surface of the quench zone. "Exposed surface" refers to the surface that is exposed to the reactants and/or reaction products. Apart from the using gold as the material of the surface of the reaction zone and optionally of the surface of the quench zone, the reactor can be of conventional design. For example, the reactor can be tubular, wherein the pyrolysis reaction occurs in the interior of the tube, and the tube can have a variety of cross-sectional shapes, such as circular, oval (elliptical) or polygonal, said shapes being of the interior or of the exterior surfaces of the tube, or both. The tubular reactor will typically have an inner diameter in the case of circular cross-section of at least about 0.125 in (0.32 cm), preferably about 0.125 in (0.32 cm) to about 3 meters, more preferably about 0.5 in (1.27 cm) to about 2 m, and most preferably about 1 in (2.54 cm) to about 1 m. The ratio of volume to surface area of the tubular reactor of unit length and interior radius R may be determined by dividing the surface area A ($A=2\pi R$) into the volume V ($V=\pi R^2$). If R is in centimeters, $V/A=(R/2)$ cm$^3$/cm$^2$. In this way it may be stated that the volume to surface ratio is at least about 0.08 cm$^3$/cm$^2$, preferably about 0.0813 cm$^3$/cm$^2$ to about 75 cm$^3$/cm$^2$, more preferably about 0.32 cm$^3$/cm$^2$, to about 50 cm$^3$/cm$^2$, and most preferably about 0.64 cm$^3$/cm$^2$ to about 25 cm$^3$/cm$^2$.

The gold on the interior surface of the reaction zone can form the entire thickness of the reactor wall, but for economy need only be a lining supported by a heat-resistant, thermally conductive material of construction, such as a metal which has a melting temperature of at least about 1100° C. and which gives structural integrity to the reactor.

Inconel® and Hastelloy® are nickel alloys suitable for use as supporting materials for the gold lining of the reactors of the invention described herein (see for example U.S. Pat. No. 5,516,947). Other thermally conductive supporting materials can be used. Thermal conductivity enables the reactor to be externally heated to provide the interior temperature necessary for the pyrolysis reaction. It is desirable that the supporting material be metallurgically bonded to the gold lining for the best heat transfer. By a metallurgical bond is meant a bond in which atoms of the metals in the supporting material and the gold lining interdiffuse, that is, diffuse among each other about the bonded interface. Normally a plurality of the tubular reactors will be positioned within a shell, and a heating medium will be flowed between the interior wall of the shell and the exterior walls of the tubular reactors bundled therein to provide the heating for the pyrolysis reaction. Alternatively, the shell can be exteriorly heated or fired by means such as electrical means to provide the interior heating. The combination of the shell and the tubular reactors positioned therein forms the pyrolysis furnace. Alternatively, the reactor may consist of a single reaction vessel, where the required heat for the reaction is other means such as hot inert gas mixed with the reactants. Use of hot inert gas to supply some or all of the heat needed for the reaction reduces or eliminates the heat that must be supplied through the reactor wall. Supplying heat through the reactor wall requires that the wall be hotter than the contents of the reaction space. This condition can lead to undesirable reactions and to decomposition of reactants, intermediates, or products at the wall. The greater the reactor cross-section, the higher wall temperatures must be to supply the necessary heat. Therefore, heating by means of hot inert gas becomes more attractive as the reactor cross-section increases.

The thickness of the gold lining is a factor in the useful life of the reactor. Deterioration of the lining is an effect of pyrolysis conditions, cleaning operations, and the diffusion of metal from the supporting material into the gold. Cleaning operations abrade the surface, resulting in loss of gold. Diffusion will eventually bring the atoms of the backing material to the surface of the reaction zone. The presence of some quantity of metals other than gold can be tolerated at the reaction surface, but when this occurs to a sufficient extent, unwanted side reactions and fouling reach the point at which replacement of the surface is necessary. The undesirable effects of cleaning and diffusion can be delayed by using a thicker gold lining, and the useful life of the reactor will thereby be greater, though the initial investment cost will also be greater. Typical gold lining thicknesses will be about 10 to about 100 mils (0.25 to 2.5 mm).

The pyrolysis reactor may be completely gold-lined, or may have unlined sections in the preheat zone, upstream of the gold-lined reaction zone of the reactor, and in the quench zone, downsteam of the gold-lined reaction zone. As stated above, the preheat zone is used to preheat the gaseous reactant feed mixture and the quench zone is used for quenching the gaseous reaction mixture to a temperature less than about 500° C. to minimize coke and /or polymer formation downstream of the reaction zone. Quenching may be accomplished by interior cooling or exterior cooling, or both.

Reactants that can produce fluoromonomers under the conditions of this invention are suitable feed materials. Preferable are mixtures of feed reactants providing both the $CF_2$: and the $CF_3CF$: or $CF_2CF_2$: moieties in the reactor that comprise a monocarbon compound and a) a dicarbon compound that in addition to atom, or b) tetrafluoroethylene, or c) perfluorocyclobutane. For example, the mixture can include chlorodifluoromethane ($CF_2HCl$) (HCFC-22), and/ or $CF_3H$ (HFC-23) to provide the $CF_2$: moiety upon pyrolysis in the reactor, and $CF_3CF_2H$ (HCFC-125), or $CF_2=CF_2$, perfluorocyclobutane (c-318), and chlorotetrafluoroethane to provide the $CF_3CF$: and/or $CF_2CF_2$: moieties. The chlorotetrafluoroethane can include $CHFClCF_3$ (HCFC-124) and $CF_2ClCF_2H$ (HCFC-124a). When chlorotetrafluoroethane is used as the dicarbon compound for feed to the reactor, HCFC-124 is preferably the major component of the dicarbon reactant, disregarding compounds that are used as inert gases and that do not undergo significant conversion in the reactor. By "major", it is meant that the mole ratio of HCFC-124:HCFC-124a is greater than about 1:1, preferably greater than about 3:2, more preferably greater than about 7:3, and most preferably greater than about 4:1. The proportion of $CF_2$: providing compound to $CF_3CF$: or $CF_2CF_2$: providing compound will preferably be about 1:5 to about 5:1 on a molar basis and more preferably 1:1. Preferred monocarbon and dicarbon compound feeds to the reactor are HCFC-22 and/or HFC-23 with HCFC-124 and HCFC-124a. HFC-23 may be used as a recycle gas in the reactor system. In this case, HFC-23 may be the major component in the reactor.

Other reactants useful under the conditions of this invention include mixtures of chlorotetrafluoroethane and perfluorocyclobutane. The molar ratio of chlorotetrafluoroethane:perfluorocyclobutane is from about 1:10 to 10:1, preferably from about 1:3 to about 3:1. The preferred mole ratios of HCFC-124:HCFC-124a are as stated above. Azeotrope or azeotrope-like mixtures of chlorotetrafluoroethane and perfluorocyclobutane as well as azeotrope or azeotrope-like mixtures of $CHClFCF_3$ with HF and/or HCl, and azeotrope or azeotrope-like mixtures of perfluorocyclobutane with HF and/or HCl can be used as at least a portion of the reactant feed. These azeotropes or azeotrope-like mixtures can be obtained, for example, as by-products from the tetrafluoroethylene manufacturing process by the thermal cleavage of chlorodifluoromethane.

Chlorotetrafluoroethane alone may be used in the synthesis of TFE, HFP, and perfluorocyclobutane. In this case, the mole ratio of HCFC-124a:HCFC-124 is at least about 9:1 and is preferably about 19:1.

Perfluorocyclobutane (c-318) may also be used with $CHF_2Cl$ (HCFC-22) to make TFE and HFP. The mole ratio of HCFC-22:c-318 is from about 9:1 to about 1:1, preferably from about 7:1 to about 1:1, most preferably from about 7:1 to about 5:3.

The effect of gold lining on the pyrolysis reaction is profound in the sense that it increases the selectivity of the reaction to form useful fluoroolefin products, notably TFE and HFP, with much-reduced formation of salts, coke, or polymer, or undesirable by-products such as PFIB or CFC-1113. The process is especially useful for making a mixture of TFE and HFP in which the TFE is at least about 30 mole %, but the process can make TFE/HFP reaction products in which the TFE content is at least about 50 mole % and preferably at least about 60 mole %. Generally, at least about 5 mole % of HFP will be present in the combined amount of TFE and HFP formed.

Preferably, the residence time in the reaction zone is less than one second, and more preferably the residence time is about 0.01 to about 0.5 seconds and even more preferably, from about 0.05 to about 0.2 seconds. Residence time is determined from the net volume of the reaction zone and the volume feed rate of the gaseous feed to the reactor at reaction temperature and pressure and refers to the amount of time a given volume of gas (containing starting materials and reaction products) remains in the reactor. As stated above, the volume of the tube forming the reaction zone is the volume of that part of the tube that is lined with gold minus any volume used as a quench zone. As the residence time is increased from these reaction times, the formation of coke, salts, and/or polymer and undesirable by-products increases. British Patent 1,062,768 discloses that at least 10 wt % of CFC-1113 is formed, based on the weight of the HFP formed, when residence times range from 0.75 to 3 seconds (Table on page 3) and that a residence time of 1 to 3 seconds is preferred (page 2, line 66). The present invention produces less than about 3 wt % of CFC-1113 based on the weight of HFP formed, and it is possible to operate the process of the present invention to produce less than about 0.01 wt %, CFC-1113, based on HFP.

Preferably, the feed gas mixture of reactants, which is at atmospheric pressure, is preheated to a temperature approaching but not at the temperature at which pyrolysis begins. Higher gas temperatures increase the formation of undesirable by-products and coke and/or polymer formation. So does higher wall temperature. Thus the closer the wall and the gas temperatures are to the desired reaction temperature, the greater will be the selectivity of useful fluoroolefins like HFP and TFE. For the case of an adiabatic reactor, the wall temperature may be lower that the gas temperature. Selectivity to useful fluoroolefins like HFP and TFE will be increased. The gas temperature within the reaction zone is considered to be the pyrolysis reaction temperature and is measured using a thermocouple in the gas phase in the reaction zone.

The reaction zone is heated to a temperature sufficient for the pyrolysis reaction to occur, preferably within the reaction time of less than one second. Thus, the walls will be heated to a temperature higher than the gaseous reactant mixture, by only about 100° C., preferably by only about 50° C. higher, and more preferably by only about 25° C., sufficiently to maximize the formation of TFE and HFP, but not so high as to negatively impact the selectivity of TFE and HFP, and increase the formation of PFIB and that of miscellaneous by-products as well as the formation of any appreciable amount of coke on the interior surface of the reaction zone and polymer in the quench zone and beyond that point in the system. It has been found that reactor temperatures of about 600° C. to about 1000° C., preferably about 700° C. to about 900° C., more preferably about 750° C. to about 850° C., and most preferably about 750° C. to about 825° C. (temperatures are measured on the outside of the reactor) obtained by exterior heating of the reactor are generally satisfactory.

The combination of residence time and temperature of the gaseous reaction mixture in the reaction zone is selected to be effective in producing a selectivity of useful fluoroolefin products like HFP and TFE of at least about 85% with the total amount of PFIB and/or CFC-1113 being less than about 5 wt %, based on the combined weight of TFE and HFP produced. More preferably, the amount of these undesired by-products is less than about 1 and about 3 wt % respectively, based on combined TFE plus HFP production and most preferably, based on the weight of HFP produced.

The smaller the amount of undesirable by-product that is formed, the better from the standpoint of treatment and disposal of the by-product, but some treatment and disposal can be tolerated for the sake of increased productivity of the useful fluoroolefins.

Coke and polymer formation, while representing a relatively minor yield loss, is a burden on economy of operation because of the need to shut-down the furnace to remove coke and/or polymer from the reactor. Thus, the yield loss attributable to coke and polymer formation is preferably no greater than 1 wt % based on TFE and HPF produced, whereby the process can be conducted for long periods of time without furnace shut-down for reactor clean out.

In one embodiment of the present invention, the gaseous feed mixture to the furnace includes an inert gas along with the reactant mixture, which inert gas is free of oxygen. As stated above, inert gas can be used to supply heat to the reaction. This is especially useful for reactors of large cross-sectional area. These, if heated solely through the walls, would require excessively high wall temperatures and this would promote undesirable reactions and fouling. Examples of inert gases which do not decrease the desired products are helium, nitrogen, hydrofluorocarbons, or perfluorocarbons that are compatible with the reaction. A compatible inert gas is one that is sufficiently stable under reaction conditions, that is, does not undergo significant self- or synergistic decomposition or reaction at about atmospheric pressure and about 850° C. with a contact time of at least one second. $CF_4$ is an example of a compatible inert gas of the perfluorocarbon type. Decomposition of less than about 5% is tolerable in an inert gas if the decomposition products do not adversely affect the desired cosynthesis of TFE and HFP. The inert gas can be incorporated into the gaseous mixture of reactants by addition thereto after the mixture is formed or by addition to one of the reactants prior to combination with the other reactant or reactants.

In another embodiment, the flow of the feed through the reactor is partially obstructed to cause back-mixing, i.e. turbulence, and thereby promote mixing of reactants and good heat transfer, further reducing the necessary residence time of the feed in the reactor, e.g. to less than about one-half second. This partial obstruction can be conveniently obtained by placing packing within the interior of the reactor, filling its entire cross-section or by using perforated baffles. The reactor packing can be particulate or fibrillar, preferably in cartridge disposition for ease of insertion and removal from the furnace, has an open structure like that of Raschig Rings or other packings with a high free volume, to avoid the accumulation of coke and to minimize pressure drop, and permits the free flow of gas, while nevertheless causing back-mixing of the gas. The free volume is the volume of the reaction zone minus the volume of the material that makes up the reactor packing. The free volume is at least about 80%, preferably at least about 90%, and more preferably about 95%. Preferably the reactor packing is composed of a material such as quartz, silicon carbide, aluminum trifluoride, or fluorided alumina. The fluorided alumina can be obtained by treating a suitable alumina, such as gamma alumina or a high density alpha alumina, with a fluoriding agent such as HF, $CHF_3$, or $CH_2F_2$ to provide a high concentration of fluoride, i.e. of greater than about 90% on the surface. One procedure for fluoriding alumina is to place the packing in a stream of $CH_2F_2$, and heat it to about 700° C. for about 4 hours. After flushing the packing with nitrogen, it is heated in air at about 600° C. for about 4 hours to remove carbon deposits.

Nano-size particles (defined herein as being about 1 to about 100 nm in diameter) of gold may be loaded onto the alpha alumina packing, for additional improved conversion and improved selectivity of HFP and TFE relative to the case of adding only fluorided packing. Such loading is preferably done after the above-mentioned fluoriding is completed. The coating method is described in the Example Section.

Increased back-mixing can also be accomplished by increasing the feed rate so as to cause turbulent flow through the reactor. The process of the present invention is usually carried out wherein the conversion per pass (average of the monocarbon and dicarbon compound feeds) is equivalent to about 20% to about 80% to obtain optimum yield of TFE and HFP.

In yet another embodiment of this reaction of $C_1$ and of $C_2$ type carbenes formed by copyrolysis, the respective reactants are preheated either as a mixture or separately. The preheat temperature should be as high as possible without causing pyrolysis. That is, less than about 1% of the reactant or reactants should be pyrolyzed during the time the reactant is at the preheat temperature. The preheat temperature depends upon the reactant, and in mixtures, upon the combination of reactants. For instance, it has been established by experiment that in the gold-lined TGA reactor (described in the Example Section as Reactor #1) that $CHF_2Cl$ begins to decompose at about 430° C. at atmospheric pressure, whereas $CHFClCF_3$ is stable to about 650° C. However, in the presence of $CHF_2Cl$, $CHFClCF_3$ begins to decompose at about 530° C., presumably because of reaction with the decomposition products of $CHF_2Cl$. Preheating the feed reduces the heat load on the reaction zone. One consequence of less heat having to be introduced through the wall of the reaction zone is that the time to reach reaction temperature will be reduced and the size of the reaction zone will therefore be reduced. Thus less gold will be needed and equipment cost will be lower.

A second consequence of preheating is that the reaction zone wall temperature can be reduced. The lower the wall temperature at a given gas pyrolysis temperature the less the formation of PFIB and other byproducts like $CF_2$=CFCl, etc. in the copyrolysis of $CHF_2Cl$ and $CHFClCF_3$.

The TFE and HFP produced are recovered and refined by techniques known to the art and the useful by-products such as HCFC-124a and perfluorocyclobutane are recycled back to the reactor to produce additional amounts of the monocarbon and dicarbon intermediates under the reaction conditions employed.

Polymerizations of TFE are well known (see e.g., U.S. Pat. No. 2,230,654 and U.S. Pat. No. 2,394,243). The production of TFE as described herein can be used as an important aspect of such polymerizations. Of note are polymerizations of TFE when subjected to super-atmospheric pressure (particularly when a catalyst is present).

Copolymerizations of TFE with other olefinic comomomers (including in some embodiments HFP), copolymerizations of HFP with other olefinic comonomers, and copolymerizations of both TFE and HFP with other olefinic comonomers are each well known. The production of TFE and/or HFP as described herein can be used as an important aspect of such copolymerizations.

Polymerizations of TFE are well known (see e.g., U.S. Pat. No. 2,230,654 and U.S. Pat. No. 2,394,243). The production of TFE as described herein can be used as an important aspect of such polymerizations. Of note are polymerizations of TFE when subjected to super-atmospheric pressure (particularly when a catalyst is present).

Copolymerizations of TFE with other olefinic comomomers (including in some embodiments HFP), copolymerizations of HFP with other olefinic comonomers, and copolymerizations of both TFE and HFP with other olefinic comonomers are each well known. The production of TFE and/or HFP as described herein can be used as an important aspect of such copolymerizations. For example, the HFP produced in the manner described herein may be copolymerized with various other olefinic compounds. Such polymerizations, especially such polymerizations catalyzed by free radical initiators, are well known in the art (see e.g., H. Mark, et al., Ed., Encyclopedia of Polymer Science and Engineering, Vol. 7, McGraw Hill Book Co., New York, 1987, p. 257-269, ibid., Vol. 16, 1989, p. 603-613, and W. Gerhartz, et al., Ed., Ullmann's Encyclopedia of Industrial Chemistry, 5$^{th}$ Ed., Vol. A11, VCH Verlagsgesellschaft mbH, Weinheim, 1988, p. 402-405 and 417-423) Useful copolymers include those with repeat units derived from one or both of tetrafluoroethylene and vinylidene fluoride, and optionally other comonomers. The polymerizations may be carried out by any method known for the copolymerization of HFP. For example, the copolymerization may be in an aqueous medium, an aqueous dispersion or emulsion, or may be carried out in supercritical $CO_2$. The particular conditions used will depend on the polymerization method chosen, and may be conventional conditions for that method. The HFP may also be copolymerized according to the processes described in U.S. Pat. No. 5,478,905 and U.S. Pat. No. 5,637,663, both of which are hereby included by reference. When used in a polymerization the HFP is preferably purified to a purity typical of HFP used as a monomer. The resulting polymers may be thermoplastics useful as molding resins, or elastomers useful in seals. In both cases the HFP-containing polymers often have good solvent, chemical and/or high temperature properties.

EXAMPLES

Three reactors were used to provide the Examples that follow. Reactor #1 is a modified TA Instruments (New Castle Del. USA) thermogravimetric analyzer (TGA) mounted horizontally and consisting of a 1 inch (2.5 cm) diameter quartz tube inside a temperature programmable computer controlled furnace. Running down the center of this tube is a quartz rod which is attached to a sensitive balance capable of weighing objects suspended from this arm to an accuracy of ~0.05 mg in the range 0-100 mg. Mounted parallel to the balance arm is a chromel/alumel thermocouple sheathed in quartz for measuring the temperature of the gases in the tube and approximating the temperature of the object being weighed. The quartz tube can be lined with a sleeve of metal foil (gold, Inconel®, etc). The exit gases are fed to a scrubber train via rubber tubing and samples for gas chromatographic GC analysis can be withdrawn by syringe through this exit tubing. Examples 1 to 7 are obtained using Reactor #1.

Reactor #2 consists of a 16 inch (40 cm) length of Hastelloy® C276 tubing. The outer diameter (OD) is 0.5 inch (1.3 cm). The tubing is lined with gold 0.030 inch (0.76 mm) thick. The inside tube diameter is 0.35 inch (089 cm). The reactor is heated using two ceramic band heaters that are clamped on the tubing to provide good contact. The first band heater, which serves as the preheater, is 12 inch (30 cm) long. The external temperature of this preheat zone of the tube is controlled with a thermocouple attached to the outside surface of the reactor at the midpoint of the 12 inch (30 cm) section. The reaction zone is a 2 inch (5 cm) section that is heated in the same manner as the preheat zone. The controlling thermocouple is placed at midpoint of the 2 inch (5 cm) section on the outside wall of the reaction zone. The empty reaction zone volume of the 2 inch (5 cm) section is 3.1 ml. At preheat and reaction temperatures, the feed and product are exposed only to the gold surface. Except as indicated, the total flow through the preheater and reactor zones is 500 ml/min and is controlled by individual mass flowmeters. Also, except as indicated, the results are obtained with the preheater control temperature set at 600° C. and reaction control temperature set at 825° C. Examples 9 to 12, 15 and 18 to 23 are obtained using the Reactor #2.

Reactor #3 is a ¾ inch (1.9 cm) ID gold-lined reactor. The reactor outer tube material is a 16 inch (40.6 cm) length Inconel® 600 (nickel alloy) tube with a wall thickness of 0.113 inch (0.29 cm) and an OD of 1.046 inch (2.7 cm). The inner tube material is gold. The wall thickness of the gold tube is 0.039 inch (0.1 cm) and the tube ID is 0.742 inch (1.9 cm). Prior to using this tube, an 8 inch (20.3 cm) portion (centered in the 16 inch (40 cm) length) is milled to an OD of ¹⁵⁄₁₆ inch (2.4 cm) so that 1 inch (2.5 cm) ID clamp-on heaters would fit snugly with enough room to position thermocouples that control and monitor temperatures. The preheat zone is 5 inch (13 cm) long and the reaction zone is 2 inch (5 cm) long. They are heated by a ceramic-type band heaters. Temperatures are controlled using thermocouples positioned at the center of each section on the outside wall of the tube. They are held securely in place by the heaters themselves. In addition, the outside wall temperatures in the reaction zone are also measured in three locations, inlet, midpoint and exit. Internal bulk-gas temperatures corresponding to these wall temperatures are also measured using a ⅛ inch (0.3 cm) OD thermocouple in a platinum sheath. Although the outside wall temperatures are not monitored in the preheat zone, the internal bulk-gas temperature is measured at four locations, one inch (2.5 cm) apart, again using an ⅛ inch (0.3 cm) OD thermocouple in a platinum sheath. Gas feeds to Reactor #3 are controlled using calibrated mass flowmeters. The reactor is operated at about 1-2 psig (108-115 kPa) back-pressure to get flow through the analytical system. Reactor #3 is used for Examples 8 and 13, 14, 16, 17 and 24-27.

Portions of the reactor effluent from Reactor #1 are analyzed off-line using a gas chromatographic/mass spectrometer (GC/MS) interface and a flame ionization detector with helium as the carrier. A small portion of the product stream from Reactors #2 and #3 is analyzed using an on-line GC/MS equipped with a 20 foot (6.1 m)×0.125 inch (3.2 mm) steel column packed with 5% Krytox® 143AC perfluoroether on 60/80 mesh (0.25/0.18 mm) Carbopak BHT. GC programming conditions are set for a start temperature of 60° C. which is held for 3 minutes. It is then heated to 200° C. at the rate of 5° C./minute and held at 200° C. for 5 minutes. The analytical results are reported in mole %. In all the examples, product analysis shows less than 0.1% PFIB unless otherwise stated.

The bulk of the reactor effluent is scrubbed in this way: The effluent gas stream is bubbled through a pair of scrubbers in series containing 10 wt % potassium hydroxide in 50% aqueous methanol. Both scrubbers have phenolphthalein as a pH indicator and are monitored for color change, which indicates that the pH is dropping. As soon as the first scrubber in the series becomes slightly acid the scrubber solution is replaced. Unless indicated, product analysis is reported in mole %. Unidentified compounds are included in the "others" rows of the tables.

Loading of the nano-size particles of gold on the alpha alumina packing is done by slurrying the packing in a solution of 0.8 g gold trichloride in 100 ml water and adding one drop HCl. The pH of the slurry is adjusted to 9.6 with sodium hydroxide solution with stirring, a solution of 1.2 g sodium citrate is added and the slurry is then left undisturbed overnight. The gold loaded packing is collected by filtration, suction dried then calcined in flowing air at 250° C. for 2 hours.

Legend

The following terminology for reactants and products is used in the Tables. The structure is given along with the code used in the Tables. In some instances, isomers are found whose identity is not certain. They are so indicated. The molecular formula is correct based on mass spectroscopy.

| | |
|---|---|
| $CHF_2Cl = 22$ | $CF_3CFHCl = 124$ |
| $CHF_3 = 23$ | $CF_2=CF_2 = TFE$ |
| $CF_3CF_2H = 125$ | $CF_3CH_2F = 134a$ |
| $CF_3CF=CF_2 = HFP$ | $CF_2Cl_2 = 12$ |
| $CF_3CH=CF_2 = 1225zc$ | $CF_2ClCF_2H = 124a$ |
| $CF_3CH_2CF_3 = 236fa$ | $CFCl_2H = 21$ |
| $C_4F_8$ isomer = 1318#1 | $CF_2ClCF_2Cl = 114$ |
| $CF_3CFCl_2 = 114a$ | F-Pentene = C5F10 |
| $C_4F_8$ isomer + PFIB = 1318#2 | $CF_2ClCF_2CF_2H = 226cb$ |
| $CF_3CFCl=CF_2 = 1215xc$ | $CF_3CFCl=CF_2 = 1215yb$ |
| $CF_3CHClCF_3 = 226da$ | $CF_3CFClCF_2Cl = 216ba$ |
| $CF_2ClCF_2CF_2 = 216ca$ | $C_4HClF_8$ isomer = 328 |
| $CF_2HCF_2CF_2Cl = 328lcc$ | $C_4H_8Cl_2$ isomer = 318#1 |
| $C_4H_8Cl_2$ isomer = 318#2 | $CClF=CF_2 = 1113$ |
| $(CF_3)_2C=CF_2 = PFIB$ | $\begin{array}{c} CF_2-CF_2 \\ \mid \quad \mid \\ CF_2-CF_2 \end{array} = c\text{-}318$ |

Example 1

Reactor #1 is used. A comparison of base metal versus noble metal materials of construction is carried out using the modified TGA apparatus described above which is lined with either Inconel® 600 or gold foils. A small coupon of the same metal is also suspended from the balance arm of the TGA such that weight loss (due to corrosion) or weight increase (due to coking) could be followed during the reaction. Table 1 lists data from comparative runs using gold and Inconel® 600 at a flow of 375:375 ml/min HCFC-22: HCFC-124 at 1 atm (100 kPa) pressure and a contact time of ~0.25 sec. In addition to the heavy coking observed in the case of the Inconel® 600 liner, the analysis of the reaction tube after the completion of the experiment reveals heavy deposits of $NiCl_2$, $CrCl_3$, and $FeCl_{2/3}$ as sublimates in the downstream cooling sections of the reactor and arising from corrosion of the Inconel® 600 component metals. As time progresses the conversion on the Inconel® stops as the reactor plugs but the gold lined reactor continues to operate in same manner as noted for 100 hours with no change. The tabulated results demonstrate the increased conversion of the feed as well as the improved selectivity to HFP+TFE.

TABLE 1

| | Gold liner | | Inconel ®-600 liner | |
|---|---|---|---|---|
| Set Temp (° C.) | 800 | 850 | 800 | 850 |
| Gas Temp (° C.) | 595 | 633 | 654 | 690 |
| Carbon Conversion (%) | 33 | 55 | 22 | 38 |
| Yield to TFE + HFP (%) | 29 | 50 | 22 | 37 |
| Yield Ratio TFE/HFP (lb/lb) | 0.9 | 0.3 | 1 | 0.4 |
| TGA results | Very light coking (<1 wt % in 6 hr) | Very light coking (<1 wt % in 6 hr) | Heavy coking and $NiCl_2$ (>5 wt % in 6 hr) | Heavy coking and $NiCl_2$ (>10 wt % in 6 hr) |

Example 2

Reactor #1 is used. A similar result to that of Example 1 is obtained when feeding 750 cc/min of HCFC-22 alone to the above mentioned TGA reactor when lined by gold or with Inconel® 600, as demonstrated in Table 2. With the Inconel® lining, heavy accumulation of salts and coke plug the reactor after a few hours. With the gold lined reactor runs free of salts and with very light coking that can be swept away by a brush, i.e. none adheres.

TABLE 2

| | Gold liner | | Inconel ®-600 liner | |
|---|---|---|---|---|
| Set Temp (° C.) | 800 | 850 | 800 | 850 |
| Gas Temp (° C.) | 574 | 604 | 627 | 674 |
| Carbon Conversion (%) | 57 | 74 | 30 | 52 |
| Yield to TFE + HFP (%) | 46 | 57 | 21 | 37 |
| Yield Ratio TFE/HFP (lb/lb) | 7 | 2.3 | 6 | 3.6 |
| TGA results | Very light coking (<1 wt % in 6 hr) | Very light coking (<1 wt % in 6 hr) | Heavy coking Heavy $NiCl_2$ (>5 wt % in 6 hr) | Heavy coking Heavy $NiCl_2$ (>10 wt % in 6 hr) |

Example 3

Reactor #1 is used. A direct comparison of the relative effects of noble metal surfaces on the pyrolysis chemistry is made using the modified TGA reactor described above. Each metal is examined as a foil liner in the quartz TGA tube. The conversions and selectivities are estimated at 250:250 ml/min flow of HCFC-22:HCFC-124 as in Table 3. Gold is the best metal, of those tested, in terms of low PFIB and other by-product production.

TABLE 3

|  | Gold | | Platinum | | Palladium | |
| --- | --- | --- | --- | --- | --- | --- |
| Set Temp (° C.) | 750 | 800 | 750 | 800 | 750 | 800 |
| Gas Temp (° C.) | 620 | 667 | 652 | 702 | 652 | 698 |
| Yield to PFIB (%) | 0.00 | 0.15 | 0.00 | 1.88 | 0.43 | 1.4 |
| Byproduct yield (%) | 0.4 | 1.6 | 5.0 | 11.9 | 3.1 | 8.4 |
| Coke Formation | 0.15 | 0.72 | 0.00 | 3.03 | 2.31 | 3.08 |

Example 4

Reactor #1 is used. Using the modified TGA reactor (without the balance arm in place), a gold-lined TGA tube is used for a comparative test wherein a flow of 375:375 ml/min HCFC-22:HCFC-124 at 1 atm (100 kPa) and a contact time of ~0.25 sec is passed through the tube. The tube is either empty or packed uniformly across its cross-section with 2 mm diameter fluoridated alumina spheres. The improved performance of the packed tube is illustrated in Table 4.

TABLE 4

|  | Empty gold tube | Gold tube packed with 2 mm spheres |
| --- | --- | --- |
| Set Temp (° C.) | 800 | 800 |
| Gas Temp (° C.) | 608 | 700 |
| Conversion HCFC-22 (%) | 63 | 90 |
| Conversion HCFC-124 (%) | 6 | 29 |
| Yield to TFE and HFP (%) | 22 | 42 |

Example 5

Reactor #1 is used. Using the modified TGA flow reactor (without the balance arm in place), a gold-lined TGA tube is used for a comparative test wherein a flow of 250 ml/min HFC-23 at 1 atm (100 kPa) is preheated to 650° C. then passed through the TGA tube at a contact time of 0.7-1.4 sec. The tube is packed uniformly across its cross-section with 12-13 mm fluoridated alpha alumina Raschig Rings (RR) with or without a loading of about nano size gold particles. The gold loading is about 1% by weight. There is an improved productivity by the gold loaded-alpha alumina packing compared with the TGA flow reactor tube packed only with alpha alumina. Table 5 summarizes the results.

TABLE 5

|  | Gold lined TGA with 12-13 mm alpha alumina RR packing | | Gold lined TGA with 1% gold loading on 12-13 mm alpha alumina RR packing | |
| --- | --- | --- | --- | --- |
| Set Temp (° C.) | 825 | 850 | 825 | 850 |
| Gas Temp (° C.) | 752 | 773 | 753 | 784 |
| Conversion of HFC-23 (%) | 27 | 41 | 36 | 58 |
| Yield to HFP (%) | 6 | 12 | 10 | 32 |
| Yield to TFE (%) | 18 | 23 | 20 | 13 |
| g PFIB/100 g HFP formed | 16.7 | 8.3 | 10. | 12.5 |

Example 6

Reactor #1 is used. The effect of residence time on by-product formation, especially of PFIB, is described in Table 6. A gold-lined TGA 20 tube is used for to test different residence time in the reactor by varying the flow rate of the feed from 500 to 1000 cc/min, all at the same volumetric ratio of HCFC-22 and HCFC-124, and all at a constant wall temperature of 800° C.

TABLE 6

| Total Flow Rate (cc/min) | 500 | 750 | 1000 |
| --- | --- | --- | --- |
| Residence time (sec) | 0.37 | 0.25 | 0.20 |
| Wall Temperature (° C.) | 800 | 800 | 800 |
| Gas Temperature (° C.) | 667 | 608 | 565 |
| Conversion of HCFC-22 (%) | 56 | 63 | 42 |
| Conversion of HCFC-124 (%) | 10 | 6 | 8.5 |
| Selectivity to HFP + TFE (%) | 84 | 89.3 | 93.2 |
| Yield ratio of TFE/HFP (lb/lb) | 1.2 | 1.5 | 1.5 |
| lb PFIB/100 lb HFP | 1.45 | BDL | BDL |
| Coke Formation, (g/min) · $10^6$ | 0.72 | none | none |
| Yield of By-Products (%) | 1.6 | 1.4 | 0.74 |

BDL = Below GC detectable limit

Example 7

Reactor #1 is used. The effect of varying the volume ratio of HCFC-22/HCFC-124 in the reactor feed on the control of by-product formation, especially of PFIB, by using the modified TGA flow reactor with a gold-lined TGA tube and a total flow rate of 750 cc/min measured at atmospheric pressure and room temperature, is described in Table 7. All tests were at the same wall temperature of 800° C.

TABLE 7

|  | HCFC-22:HCFC-124 Volume Ratio | | |
| --- | --- | --- | --- |
|  | 4:1 | 1:1 | 2:3 |
| Wall Temperature (° C.) | 800 | 800 | 800 |
| Gas Temperature (° C.) | 488 | 608 | 628 |
| Conversion of HCFC-22% | 54 | 63 | 46 |
| Conversion of HCFC-124% | 19 | 6 | 4 |
| Selectivity to HFP + TFE % | 83 | 89 | 89.5 |
| Yield ratio of TFE/HFP (lb/lb) | 4.7 | 1.5 | 1.3 |
| lb PFIB/100 lb HFP | BDL | BDL | BDL |
| Coke Formation, (g/min) · $10^6$ | 1.6 | none | 0.55 |
| Yield of By-Products % | 5.2 | 1.4 | 0.83 |

BDL = Below GC detectable limit

Example 8

Reactor #3 is used. The effect of temperature on the copyrolysis of HCFC-22 and HCFC-124 in a gold lined reactor is summarized in Table 8 at a constant combined flow rate of 800 cc/min at a respective ratio of 3:2 when the reactor control temperature is varied from 750° C. to 850° C. and the preheat wall temperature is controlled to 550° C. at the 3 inch (76 mm) point of the 5 inch (127 mm) long preheater that directly precedes the 2 inch (51 mm) long reactor section.

TABLE 8

| Preheat set Temperature (° C.) | 550 | 550 | 550 |
|---|---|---|---|
| Preheat gas Temperature (° C.) | 503 | 515 | 526 |
| Reactor Middle Wall Temperature (° C.) | 749 | 799 | 840 |
| Reactor Middle Gas Temperature (° C.) | 667 | 706 | 739 |
| Conversion of HCFC-22 (%) | 43.9 | 69.2 | 84.1 |
| Conversion of HCFC-124 (%) | −0.7 | −2.3 | 14.2 |
| Selectivity to HFP + TFE (%) | 89.4 | 83.5 | 75.6 |
| Yield ratio of TFE/HFP (lb/lb) | 7.2 | 2.6 | 0.8 |
| lb PFIB/100 lb HFP | $1.3 \cdot 10^{-4}$ | $1.4 \cdot 10^{-4}$ | 0.02 |
| By-Products (%) | 2.8 | 6.7 | 13.6 |

Example 9

Reactor #2 is used. Table 9 summarizes data obtained when either HCFC-22 or HCFC-124 is subjected to thermolysis by itself. The temperatures are presented in the form xxx/yyy; xxx being the outside wall temperature and yyy being the temperature in the gas phase in the reactor. In this example, only the wall temperature is recorded. With HCFC-22 as the feed, high yields of TFE are produced. However, with HCFC-124 as the feed, the conversion and yield are low and the major product is HFP.

TABLE 9

| Preheat zone (° C.) | 600/— | 600/— |
|---|---|---|
| Reaction zone Inlet (° C.) | 791/— | 792/— |
| Reaction zone Center (° C.) | 820/— | 816/— |
| Reaction zone Outlet (° C.) | 789/— | 783/— |
| HCFC-22 (cc/min) | 500 | 0 |
| HCFC-124 (cc/min) | 0 | 500 |
| Results (mole %) | | |
| TFE | 40.6 | 0.4 |
| HFP | 2.2 | 1.5 |
| HCFC-22 | 44.6 | 0.1 |
| HCFC-124a | 4.8 | 0.3 |
| HCFC-124/c-318 | 4.5 | 94.1 |
| Others | 3.4 | 3.6 |
| Mole Ratio | | |
| (HFP/(TFE + HFP)) × 100 | 5.0 | 77.9 |

Example 10

Reactor #2 is used. Table 10 provides data obtained when HCFC-124 alone is subjected to thermolysis at different contact times by varying the flow of HCFC-124. Again, HFP is observed as the main product and the yields are low.

TABLE 10

| Preheat zone (° C.) | 600/— | 600/— | 600/— |
|---|---|---|---|
| Reaction zone Inlet (° C.) | 796/— | 795/— | 794/— |
| Reaction zone Center (° C.) | 821/— | 821/— | 821/— |
| Reaction zone Outlet (° C.) | 795/— | 794/— | 794/— |
| HCFC-22 feed (cc/min) | 0 | 0 | 0 |
| HCFC-124 feed (cc/min) | 100 | 200 | 400 |
| Results (mole %) | | | |
| TFE | 0.5 | 0.6 | 0.5 |
| HFP | 14.7 | 5.6 | 2.1 |
| HCFC-22 | 0.7 | 0.4 | 0.2 |
| HCFC-124a | 1.6 | 0.7 | 0.4 |
| HCFC-124 + c-318 | 54.8 | 81.2 | 92.0 |
| Others | 27.7 | 11.5 | 4.9 |
| Mole Ratio | | | |
| (HFP/(TFE + HFP)) × 100 | 96.6 | 89.9 | 81.4 |

Example 11

Reactor #2 is used. Table 11 provides data obtained when mixtures of HCFC-22 and HCFC-124 are employed. The amount of HFP relative to TFE is high. In this run, internal bulk gas temperatures corresponding to the outside wall temperature are also monitored. Thus in column 2, in the pair 731/609, the first number refers to the outside wall temperature in ° C. and the second number refers to the corresponding bulk gas temperature in ° C. monitored by a multipoint platinum-sheathed thermocouple. Both PFIB and CTFE are below the detection limit of 0.1% of the reactor effluent in these reactions.

TABLE 11

| Preheat zone (° C.) | None | None | None | None | None |
|---|---|---|---|---|---|
| Reaction zone Inlet (° C.) | 731/609 | 786/662 | 832/703 | 786/690 | 835/732 |
| Reaction zone Center (° C.) | 746/674 | 796/726 | 846/775 | 795/749 | 845/801 |
| Reaction zone Outlet (° C.) | 756/672 | 808/724 | 858/778 | 809/743 | 863/792 |
| HCFC-22 feed (cc/min) | 200 | 200 | 200 | 100 | 100 |
| HCFC-124 feed (cc/min) | 100 | 100 | 100 | 100 | 100 |
| Results (mole %) | | | | | |
| TFE | 13.6 | 23.9 | 19.3 | 14.5 | 4.5 |
| HFP | 0.7 | 4.0 | 18.9 | 13.7 | 39.9 |
| HCFC-22 | 50.8 | 27.6 | 14.2 | 10.1 | 5.8 |
| HCFC-124a | 0.3 | 1.7 | 5.7 | 2.9 | 5.0 |
| HCFC-124 + c-318 | 34.0 | 40.7 | 34.4 | 53.8 | 27.3 |
| Others | 2.6 | 4.9 | 13.4 | 8.1 | 22.6 |
| Mole Ratio | | | | | |
| (HFP/(TFE + HFP)) × 100 | 4.8 | 14.3 | 49.5 | 48.6 | 89.9 |

Example 12

Reactor #2 is used, operating at a control temperature of 825° C. with the preheater operating at a control temperature of 600° C. The feed is a mixture of HCFC-124 (250 cc/min), HCFC-22 (150 cc/min) and perfluorocyclobutane (100 cc/min). Product analysis is summarized in Table 12.

TABLE 12

| Preheat zone (° C.) | 600 |
|---|---|
| Reaction zone Center (° C.) | 825 |
| HCFC-22 feed (cc/min) | 150 |
| HCFC-124 feed (cc/min) | 250 |
| c-318 (cc/min) | 150 |
| Results (mole %) | |
| TFE | 16.0 |
| HFP | 6.7 |
| HCFC-22 | 7.0 |
| HCFC-124/c-318 | 45.8/21.2 |

TABLE 12-continued

| Mole Ratio | |
|---|---|
| (HFP/(TFE + HFP)) × 100 | 29.4 |

Example 13

Reactor #3 is used. At a control temperature of 750° C., a mixture of HCFC-22 and HCFC-124 are passed at varying ratios. Product analysis is summarized in Table 13. Here also, the amounts of PFIB and CTFE are below 0.01 %.

TABLE 13

| Preheat zone Control setting (° C.) | 550 | 550 | 550 |
|---|---|---|---|
| Preheat zone gas temp (° C.) | 500 | 499 | 445 |
| Reaction zone Control setting (° C.) | 750 | 750 | 750 |
| Reaction zone Middle wall/gas (° C.) | 741/654 | 742/658 | 742/643 |
| HCFC-22 feed (cc/min) | 800 | 500 | 200 |
| HCFC-124 feed (cc/min) | 200 | 500 | 800 |
| Results (mole %) | | | |
| TFE | 12.2 | 9.2 | 2.8 |
| HFP | 0.4 | 0.7 | 0.5 |
| HCFC-22 | 64.7 | 38.3 | 11.5 |
| HCFC-124 | 21.7 | 51.1 | 84.8 |
| Others | 0.9 | 0.1 | 0.4 |

Example 14

Reactor #3 is used. Example 13 is substantially repeated except that the operating control temperature is 850°0 C. The results are summarized in Table 14. In this instance, the peak identified as FC-1318#2 contains some PFIB as determined by mass spectrometry. The PFIB co-elutes with another isomer of the same molecular formula, and based on mass spectrometry it is established that about 50 to 60% of the 1318#2 found is PFIB.

TABLE 14

| Preheat zone Control setting (° C.) | 550 | 550 | 550 |
|---|---|---|---|
| Preheat zone Gas (° C.) | 525 | 531 | 490 |
| Reaction zone Control setting (° C.) | 850 | 850 | 850 |
| Reaction zone Middle wall (° C.) | 852 | 844 | 836 |
| Reaction zone Middle gas (° C.) | 735 | 733 | 723 |
| HCFC-22 feed (cc/min) | 800 | 500 | 200 |
| HCFC-124 feed (cc/min) | 200 | 500 | 800 |
| Results (mole %) | | | |
| TFE | 26.7 | 15.1 | 4.1 |
| HFP | 7.3 | 10.3 | 6.0 |
| HCFC-22 | 28.5 | 13.5 | 3.4 |
| HCFC-124 | 29.3 | 55.6 | 83.9 |
| FC-1318#2 | 0.1 | 0.2 | 0.1 |
| Others | 7.9 | 5.6 | 2.5 |

Examples 15-17

Reactor #2 is used for Example 15, which shows the result of pyrolysis of HCFC-124 and c-318 at ~815° C. reaction zone center temperature. Reactor #3 is used for Example 16, pyrolysis of a HCFC-124:c-318 mixture, and Example 17, pyrolysis of a HCFC-124a:c-318 mixture, both at ~700° C. reaction zone center temperature. The analytical results are reported in mole %. In the examples, product analysis shows less than 0.1% PFIB. The reaction results are summarized in Tables 15 and 16.

TABLE 15

| | Example No. 15 |
|---|---|
| Preheat zone (° C.) | 610 |
| Reaction zone Inlet (° C.) | 788 |
| Reaction zone Center (° C.) | 814 |
| Reaction zone Outlet (° C.) | 777 |
| HCFC-124 feed (cc/min) | 300 |
| c-318 feed (cc/min) | 200 |
| Results (mole %) | |
| TFE | 11.9 |
| HFP | 5.2 |
| HCFC-124 | 51.4 |
| HCFC-124a | 0.4 |
| c-318 | 28.7 |
| HCFC-22 | 0.6 |
| Others | 1.9 |

TABLE 16

| | Example No. | |
|---|---|---|
| | 16 | 17 |
| Preheat zone Center (° C.) | 494 | 492 |
| Reaction zone Center (° C.) | 694 | 693 |
| HCFC-124 feed (cc/min) | 400 | 0 |
| HCFC-124a feed (cc/min) | 0 | 400 |
| c-318 feed (cc/min) | 400 | 400 |
| Results (mole %) | | |
| TFE | 4.2 | 9.7 |
| HFP | 0.6 | 0.5 |
| HCFC-124 | 45.3 | — |
| HCFC-124a | 0.3 | 49.2 |
| c-318 | 49.1 | 39.2 |
| HCFC-22 | 0.1 | 0.7 |
| Others | 0.4 | 0.8 |

PFIB and CFC-1113 are both below the detection limit of about 0.1 mole % in the reactor effluent.

Examples 18-25

Reactor #2 is used for Examples 18 to 23. Reactor #3 is used for Examples 24 and 25. Analytical results are reported in mole %. The results are summarized in Tables 17 and 18.

Examples 18 to 22 show the effect of inert gas addition on the pyrolysis of HCFC-124. Total feed gas volume is kept constant. The production of TFE and HFP increases as the ratio of inert gas to HCFC-124 increases.

Examples 22 and 23 show that HCFC-124a is more selective in forming TFE compared to HFP and gives TFE in much greater amount. Comparison of the results shows that 124a is more reactive and more selective to products of interest than is 124. Examples 24 and 25 (Table 18) show the results of pyrolysis of HCFC-124a at temperatures of about 650° C. and 750° C.

TABLE 17

| | Example No. | | | | | |
|---|---|---|---|---|---|---|
| | 18 | 19 | 20 | 21 | 22 | 23 |
| Preheat zone set temp. (° C.) | 600 | 600 | 600 | 600 | 600 | 600 |
| Reaction zone Inlet (° C.) | 792 | 790 | 791 | 791 | 792 | 790 |
| Reaction zone Center (° C.) | 816 | 816 | 816 | 816 | 816 | 815 |

TABLE 17-continued

|  | Example No. | | | | | |
| --- | --- | --- | --- | --- | --- | --- |
|  | 18 | 19 | 20 | 21 | 22 | 23 |
| Reaction zone Outlet (° C.) | 783 | 782 | 781 | 781 | 779 | 779 |
| HCFC-124 feed (cc/min) | 500 | 400 | 300 | 200 | 100 | 0 |
| HCFC-124a feed (cc/min) | 0 | 0 | 0 | 0 | 0 | 100 |
| Helium feed (cc/min) | 0 | 100 | 200 | 300 | 400 | 400 |
| Results (mole %) | | | | | | |
| TFE | 0.4 | 0.5 | 0.7 | 1.0 | 1.5 | 44.9 |
| HFP | 1.5 | 1.6 | 2.4 | 3.0 | 4.3 | 3.2 |
| HCFC-124 | 94.1 | 94.0 | 92.1 | 90.5 | 87.8 | 4.3 |
| HCFC-124a* | 0.3 | 0.4 | 0.4 | 0.5 | 0.6 | 39.9 |
| HCFC-22 | 0.1 | 0.1 | 0.2 | 0.2 | 0.2 | 4.8 |
| HFC-23 | 0.3 | 0.3 | 0.4 | 0.5 | 0.6 | 0.2 |
| HFC-134a | 0.5 | 0.4 | 0.5 | 0.5 | 0.4 | <0.1 |
| Others | 2.8 | 2.8 | 3.4 | 3.9 | 4.5 | 2.8 |

*The 124a contains some c-318

TABLE 18

|  | Example No. | |
| --- | --- | --- |
|  | 24 | 25 |
| Preheat zone Center (° C.) | 574 | 629 |
| Reaction zone Inlet (° C.) | 623 | 708 |
| Reaction zone Center (° C.) | 646 | 753 |
| Reaction zone Outlet (° C.) | 642 | 759 |
| HCFC-124a feed (cc/min) | 400 | 400 |
| Results (mole %) | | |
| TFE | 5.4 | 29.1 |
| HFP | 0.1 | 12.1 |
| HCFC-124 | 2.8 | 0 |
| HCFC-124a | 90.8 | 29.9 |
| HCFC-22 | 0.4 | 11.9 |
| c-318 | 0 | 8.5 |
| CFC-114 | 0.3 | 0.8 |
| HCFC-226cb | <0.1 | 1.2 |
| PFIB* | <0.1 | 0.7 |
| Others | 0.2 | 5.2 |

*The PFIB contains some 1318s.

Examples 26 and 27

Reactor #3 is used for Examples 26 and 27. HCFC-22: c-318 mixture is pyrolyzed at 720° C. and 746° C. Analytical results are reported in mole %. The reaction results are summarized in Table 19.

TABLE 19

|  | Example No. | |
| --- | --- | --- |
|  | 26 | 27 |
| Preheat zone Center (° C.) | 548 | 554 |
| Reaction zone Center (° C.) | 720 | 746 |
| HCFC-22 feed (cc/min) | 600 | 600 |
| c-318 feed (cc/min) | 200 | 200 |
| Results (mole %) | | |
| TFE | 33.3 | 36.4 |
| HFP | 2.5 | 6.0 |
| HCFC-124a | 5.8 | 9.6 |
| HCFC-22 | 33.0 | 22.7 |
| c-318 | 22.0 | 20.0 |
| HCFC-226cb | 1.5 | 1.7 |

TABLE 19-continued

|  | Example No. | |
| --- | --- | --- |
|  | 26 | 27 |
| PFIB | 0.1 | 0.2 |
| Others | 1.3 | 2.2 |

The data disclosed above demonstrates the profound effects of utilizing a gold-lined reaction zone for the production of fluorocarbon monomer materials.

Example 28

This example describes the production of a tube of Inconel® 600 alloy with a lining of gold according to a preferred embodiment of this invention. The Inconel® tube is the supporting material. The Inconel® tube has an outer diameter of 26.7 mm and an inner diameter of 20.9 mm and is less than one meter long. The gold lining is a wrought tube of the same length, having an outer diameter of 20.50 mm and an inner diameter of 18.50 mm. The inner surface of the Inconel® tube is honed to a finish of RMS 8 and cleaned by first degreasing with hot Oakite #3 soap solution. This is followed by acid pickling using a solution of sulfuric acid and hydrochloric acid (mixed in proportions of 7.9% by volume 93% sulfuric acid, 12% by volume 32% hydrochloric acid, the balance water). The pickling time is 10 to 20 minutes. The tube is then rinsed with deionized water for 0.5 to 1 minute. The tube is then pickled in aqueous nitric acid, (made by mixing 20% by volume of 68% nitric acid in 80% by volume of water) for 20 minutes. This is followed by rinsing with deionized water for 0.5 to 1 minute and drying. The tube is inspected visually and the pickling steps are repeated if any unusual areas are seen.

The gold tube is prepared by degreasing with an appropriate solvent, followed by acid cleaning with nitric acid (an aqueous solution made 20% by volume of 68% nitric acid in water) for 20 minutes. This is followed by rinsing with deionized water for 0.5 to 1 minute and drying.

The gold lining is swaged onto a mandrel and pulled into the Inconel® tube. The lining is then mechanically expanded by drawing an expansion plug or mandrel through the gold lining. Increasingly larger expansion plugs are dawn through the gold lining until the calculated outer diameter of the gold lining is within the tolerances of the inner diameter of the Inconel® tube. The combined Inconel®-gold structure is referred to as "the tube".

The seams between the gold and Inconel® at each end of the tube are sealed using a nickel braze. At intervals along the tube holes are drilled through the Inconel® layer only and fittings are attached to allow the evacuation of the space between the gold layer and the Inconel® layer. The space is evacuated. The tube is then filled with water, and hydrostatic pressure of 20 MPa is applied at room temperature for several hours. The pressure is relieved and the tube drained and dried. The tube is then pressurized with an inert gas such as argon to about 700 kPa and heated to 1050° K to 1150° K for about 8 hours. After cooling and depressurization the tube is tested to determine the extent of bonding (the ultrasonic test does not measure the quality of the bond—it determines whether a bond is present). Ultrasonic testing on this tube indicates that there is bonding on over 99% of the tube surface. Metallographic cross-sections of the tube are prepared and it is confirmed that the gold liner is bonded to the Inconel®. There is no evidence of contamination at the gold-Inconel® interface. Elemental profiles are measured and it is determined that the bond extends over about 250 μm in the radial direction, approximately centered on what had been the interface between the gold lining and the Inconel® tube when they were first assembled. This bonding distance is measured from the point at which the gold content is first seen to decline from 100 atom %, i.e. pure gold, to the point at which the gold content is first seen to reach 0 atom %. This confirms the interdiffusion of the gold and the supporting Inconel®, and shows that the bond between the gold and Inconel® is a metallurgical bond.

What is claimed is:

1. A process for producing at least one fluoroolefin selected from the group consisting of tetrafluoroethylene and hexafluoropropylene, comprising pyrolyzing at least one compound selected from the group consisting of fluoroform, chlorodifluoromethane, chlorotetrafluoroethane, a mixture of chlorodifluoromethane and chlorotetrafluoroethane, and a mixture of chlorodifluoromethane and perfluorocyclobutane, to obtain said at least one fluoroolefin, said pyrolyzing being carried out in a tubular reactor at a temperature of about 600° C. to 1000° C., the interior surface of said reactor being a supported lining comprising gold.

2. The process of claim 1 wherein the inner diameter of said reactor is at least about 1 in (2.54 cm).

3. The process of claim 1 wherein said process produces a mixture of said tetrafluoroethylene and hexafluoropropylene, wherein said tetrafluoroethylene constitutes at least about 50 mol % of said mixture.

4. The process of claim 1 wherein said at least one compound consists essentially of chlorodifluoromethane or fluoroform.

5. The process of claim 1 wherein said at least one compound consists essentially of $C_2HClF_4$ containing a molar ratio of $CHF_2CClF_2$ to $CHClFCF_3$ of at least about 9:1.

6. The process of claim 1 wherein said at least one compound consists essentially of $C_2HClF_4$ and perfluorocyclobutane in a molar ratio of $C_2HClF_4$ to perfluorocyclobutane from about 1:10 to about 10:1, and wherein said $C_2HClF_4$ contains $CHClFCF_3$ and $CHF_2CClF_2$ in a molar of at least about 1:1.

7. The process of claim 1 wherein both said tetrafluoroethylene and said hexafluoropropylene are produced in a combined yield of at least about 85%.

8. The process of claim 1 wherein said reactor further comprises a quench zone, the surface of which comprises gold.

9. The process of claim 1 wherein said conditions include temperature and residence time selected to produce a product containing less than about 1 mole % perfluoroisobutylene.

10. The process of claim 1 wherein said compound has a residence time in the reaction zone of no more then about one second.

11. The process of claim 1 wherein at least one of said at least one compound is preheated to a temperature less then its pyrolysis temperature.

12. The process of claim 1 wherein said compound is fed to said reactor as a gaseous mixture of said at least one compound and an inert gas which is free of oxygen and hydrogen.

13. The process of claim 1 further comprising turbulent flowing of said compound in said reaction zone.

14. The process of claim 13 further creating obstructions in the reaction zone to cause said turbulent flowing.

* * * * *